US008715246B2

(12) United States Patent
Giambattista et al.

(10) Patent No.: US 8,715,246 B2
(45) Date of Patent: May 6, 2014

(54) MEDICAMENT CONTAINER HOLDER ARRANGEMENT

(75) Inventors: Lucio Giambattista, East Hanover, NJ (US); Antonio Bendek, Vernon, NJ (US)

(73) Assignee: SHL Group AB, Nacka Strand (SE)

( * ) Notice: Subject to any disclaimer, the term of this patent is extended or adjusted under 35 U.S.C. 154(b) by 16 days.

(21) Appl. No.: 13/378,933

(22) PCT Filed: Jul. 15, 2010

(86) PCT No.: PCT/SE2010/050846
§ 371 (c)(1),
(2), (4) Date: Feb. 16, 2012

(87) PCT Pub. No.: WO2010/147553
PCT Pub. Date: Dec. 23, 2010

(65) Prior Publication Data
US 2012/0143143 A1 Jun. 7, 2012

Related U.S. Application Data

(60) Provisional application No. 61/187,950, filed on Jun. 17, 2009.

(30) Foreign Application Priority Data

Jul. 31, 2009 (SE) ........................................ 0950574

(51) Int. Cl.
*A61M 5/32* (2006.01)

(52) U.S. Cl.
USPC ............................. 604/192; 604/207; 604/221

(58) Field of Classification Search
USPC ................. 604/207–210, 220–221, 223, 187, 604/192–193
See application file for complete search history.

(56) References Cited

U.S. PATENT DOCUMENTS 4,986,818 A 1/1991 Imbert et al.
(Continued)

FOREIGN PATENT DOCUMENTS

WO 2010/147553 A1 12/2010

OTHER PUBLICATIONS

Request to Restore Priority in PCT/2010/050846, Jul. 15, 2010.
Swedish Patent Office, Notice of Intended Refusal of Request to Restore Priority in PCT/2010/050846, Jul. 19, 2010.

(Continued)

*Primary Examiner* — Quynh-Nhu H Vu
(74) *Attorney, Agent, or Firm* — Piedmont Intellectual Property (57) ABSTRACT

The present invention relates to a medicament container holder arrangement comprising a medicament container holder 16 and a medicament container 18 wherein the medicament container holder 16 is provided with distally arranged support surfaces 25 for flanges 24 arranged on a distal part of the medicament container 18 to be placed in said medicament container holder 16, which medicament container 18 is arranged with a needle shield 20 to the proximal end thereof, wherein said needle shield 20 has a diameter generally equal or larger than the diameter of said medicament container 18, wherein said medicament container holder arrangement further comprises holders arranged on the container holder for holding said medicament container 18 around a proximal shoulder portion 22 thereof and a resilient support element 23 arranged between the flanges 24 and the support surfaces 25 whereby the holders and the resilient support element 23 absorb and spread forces between the medicament container and the container holder.

16 Claims, 5 Drawing Sheets

(56) References Cited

U.S. PATENT DOCUMENTS

| | | |
|---|---|---|
| 5,147,325 A | 9/1992 | Mitchell et al. |
| 5,215,535 A | 6/1993 | Gettig et al. |
| 5,855,839 A * | 1/1999 | Brunel .......................... 264/524 |
| 8,021,335 B2 * | 9/2011 | Lesch, Jr. ....................... 604/135 |
| 2009/0254044 A1 | 10/2009 | Kohlbrenner et al. |

OTHER PUBLICATIONS

Swedish Patent Office, Decision on Request to Restore Priority in PCT/2010/050846, Sep. 27, 2010.

Swedish Patent Office, Int'l Search Report in PCT/SE2010/050846, Sep. 21, 2010.

Swedish Patent Office, Written Opinion in PCT/SE2010/050846, Sep. 21, 2010.

* cited by examiner

MEDICAMENT CONTAINER HOLDER ARRANGEMENT

TECHNICAL AREA

The present invention relates to a medicament container holder arrangement to be used in a medicament delivery device and in particular a medicament container holder arrangement that is capable of preventing containers e.g. cartridges, syringes or the like from breaking during medicament delivery.

TECHNICAL BACKGROUND

There are a number of medicament delivery devices on the market in which a medicament container is placed, usually in an appropriate container holder designed to accommodate a certain type and size of the medicament container.

Further, there are a number of different medicament containers on the market, such as the common syringe type having laterally extending flanges at the distal part thereof, which flanges act as stop members against longitudinal movement, and cartridges having a proximal neck portion, onto which a needle may be attached, which cartridges normally are supported against a shoulder surrounding said neck portion. Almost all of the syringes and cartridges on the market are manufactured from glass, being a very suitable material that will not react with the medicament, does not age and can readily be sterilized.

Lately a new type of needle shield has been developed, which is commonly called Rigid Needle Shield or RNS. The RNS comprises a cap which has a hard, semi-transparent plastic shell, with a soft and flexible inner core which protects a syringe needle. The soft core is made of thermoplastic elastomer (TPE), into which the needle sticks to protect it from damage whilst also providing a sterile seal.

The cap has very often generally the same diameter as the cartridge onto which it is connected; thereby the cartridge has to be provided with flange members at the distal part of the container. It is not uncommon that glass medicament containers break during e.g. an injection process due to the high forces that are produced from medicament delivery force members, such as injection springs, acting on plunger rods, which in turn are intended to push stoppers inside the medicament containers for expelling medicament.

Other possible causes where the medicament containers may break are during a penetration process. It is of course also possible that a medicament container may break if the medicament delivery device is dropped on a hard surface.

When using so called rigid needle shields, since they have generally substantially the same diameter as the medicament containers on which they are mounted, when placed in a medicament container holder, they are difficult to support at a proximal shoulder portion of the container.

This in turn means that if the medicament container breaks for some reason, pieces of the container will fall out through the proximal opening of the device because there is nothing in the proximal area that is holding the medicament container. There is thus a risk that persons may be injured by broken glass from the medicament container.

WO 2007/08115 discloses an autoinjector wherein a medicament container with a needle and a needle cover is placed in a container holder that supports the container at the front using flexible arms that grip the container in the gap between the needle cover and a shoulder portion of the container. The support is intended to prevent breakage or to stop broken pieces from falling out of the container holder. No support is provided at the rear flanges of the container.

However, experience has shown that it is not always enough to support a container or syringe only at the shoulder portion or at the rear flange in order to prevent it from breaking. Fluids of high viscosity necessitate stronger driving forces for ejecting medicament. Consequently the syringe or cartridge is subjected to greater forces, resulting in increased risk of breakage.

BRIEF DESCRIPTION OF THE INVENTION

A main aim of the present invention is to remedy the drawbacks associated with medicament containers provided with RNS.

This aim is obtained by the features of the independent patent claim. Preferable embodiments of the invention form the subject of the dependent patent claims. According to a main aspect of the invention it is characterised by a medicament container holder arrangement intended to be used in a medicament delivery device, comprising a medicament container holder and a medicament container wherein the medicament container holder is provided with distally arranged support surfaces for flanges arranged on a distal part of the medicament container to be placed in said medicament container holder, which medicament container is arranged with a needle shield to the proximal end thereof, wherein said needle shield has a diameter generally equal or larger than the diameter of said medicament container, characterised in that said medicament container holder arrangement further comprises holders arranged on the container holder for holding said medicament container around a proximal shoulder portion thereof and a resilient support element arranged between the flanges and the support surfaces whereby the holders and the resilient support element absorb and spread forces between the medicament container and the container holder.

According to another aspect of the invention said resilient support element is manufactured from a flexible material, such as TPE.

According to another aspect of the invention said resilient support member is in the form of a ring arranged around the medicament container, adjacently a proximal surface of the flanges.

According to another aspect of the invention said resilient support member is in the form of a cushioning element integrally attached to the support surfaces.

According to a further aspect of the invention said holders comprise flexible arms arranged such that, when a medicament container is placed in said medicament container holder from the distal end thereof and pushed forward such that said needle shield comes in contact with the flexible arms, the latter are capable of flexing outwardly, permitting passage of said needle shield, and then capable of flexing inwardly after passage of said needle shield.

According to yet another aspect of the invention said flexible arms are provided by through-going U-shaped slits on the longitudinal extending surface of the holder.

According to another aspect of the invention said flexible arms further comprise inwardly directed ledges capable of being placed in contact with said shoulder portion of said medicament container.

According to another aspect of the invention said holders further comprise outwardly directed ledges cooperating with a housing part of said medicament delivery device such that, when the container holder is positioned inside said housing part, said flexible members are prevented from flexing radially outwards, thereby firmly holding said medicament container.

There are a number of advantages with the present invention. The support surfaces, together with the support element, abut against the flanges of the container and the holders grip the container at the front. Together they divide the forces acting on the container during medicament delivery to prevent the container from breaking.

Due to the holders arranged on the medicament container holder, the medicament container, or parts of it, are prevented from moving further in the proximal direction should the distally arranged flanges no longer be able of holding the medicament container, due for example by breakage of the medicament container.

Because the holders preferably are radially flexible it is possible to pass the rigid needle shield of the medicament container when placing the latter in the medicament container holder. Since also the members preferably have inwardly directed ledges, a good hold of the neck portion of the medicament container is obtained.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

The present invention relates to a medicament container holder arrangement comprising a medicament container holder 16 and a medicament container 18 wherein the medicament container holder 16 is provided with distally arranged support surfaces 25 for flanges 24 arranged on a distal part of the medicament container 18 to be placed in said medicament container holder 16, which medicament container 18 is arranged with a needle shield 20 to the proximal end thereof, wherein said needle shield 20 has a diameter generally equal or larger than the diameter of said medicament container 18, wherein said medicament container holder arrangement further comprises holders arranged on the container holder for holding said medicament container 18 around a proximal shoulder portion 22 thereof and a resilient support element 23 arranged between the flanges 24 and the support surfaces 25 whereby the holders and the resilient support element 23 absorb and spread forces between the medicament container and the container holder.

Figure 1:
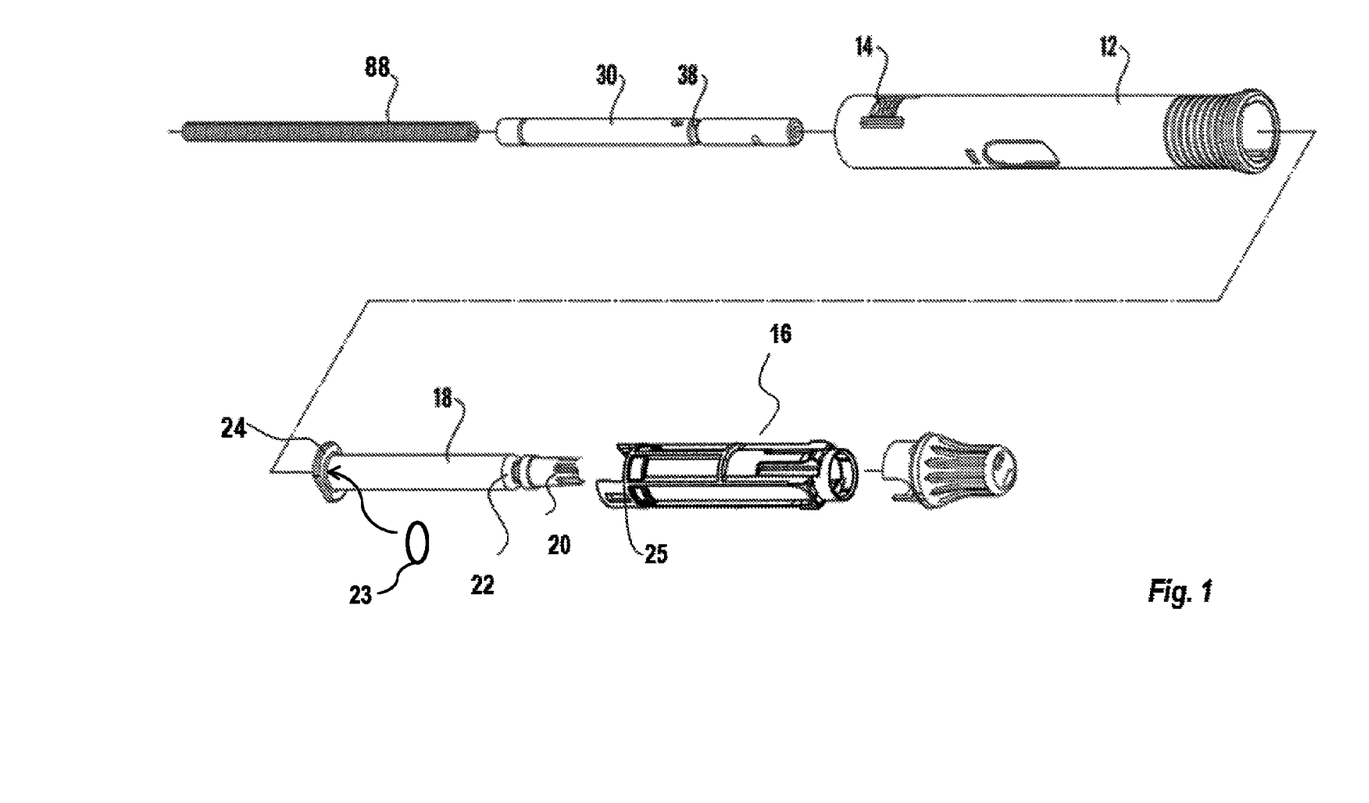
FIG. 1 shows an exploded view of a proximal part of a medicament delivery device provided with a medicament container holder according to the present invention.

A medicament delivery device 8 comprising the present invention comprises a generally tubular outer housing 10. In the proximal end of the housing, to the right in FIG. 1, a generally tubular needle shield 12 is arranged slidably in the outer housing. When in a non-extended position the needle shield is held in place by protrusions 14 on the outer surface co-operating with ledges (not shown) on an inner surface of the housing 10. Inside the needle shield in the proximal area of the device, the medicament container holder 16 is arranged, which will be described in more detail below. Inside the medicament container holder 16 the medicament container 18, containing medicament, is arranged. The medicament container is provided with a so called rigid needle shield RNS 20 attached to a proximal neck portion of the medicament container 18, which neck portion transforms into a shoulder portion 22. The needle shield 20 has a diameter generally equal or larger than the diameter of said medicament container 18. The distal end of the medicament container is provided with outwardly directed flanges 24. Since the flanges are usually not designed to withstand large loads, the resilient support element 23, made of a flexible material such as TPE, is arranged between a proximal surface of the flanges 24 and a support surface 25 of at the distal end of the container holder 16, for absorbing and spreading forces between the flanges 24 and the support surfaces 25. The resilient support element 23 may be in the form of a collar arranged adjacently a proximal surface of the flanges 24. Alternatively it may be in the form of a cushioning element integrally attached to the support surfaces 25.

Figure 2:
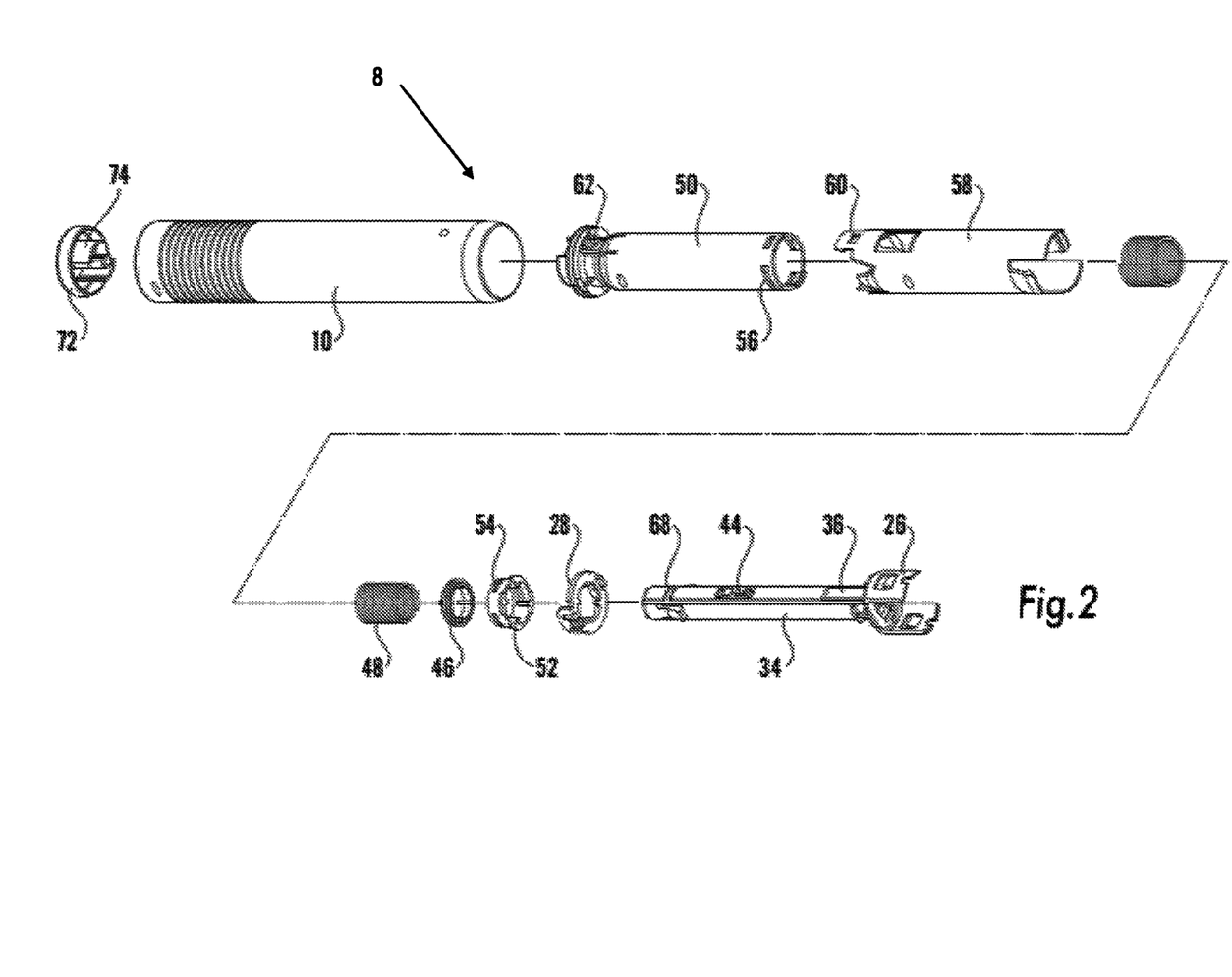
FIG. 2 shows an exploded view of a distal part of the medicament delivery device of FIG. 1.

A generally elongated plunger rod 30 extends into the medicament container 18 with one end adjacent a stopper positioned inside the medicament container. The distal end of the plunger rod 30 is surrounded by an activation housing 34 which is snap-fitted to the medicament container holder 16 through a holder 26 which is a part of the activation housing. The activation housing 34 is arranged with flexible tongues 36, where each tongue is arranged with inwardly directed ledges. In an initial state, these ledges are positioned in a circumferential groove 38 on the plunger rod 30. The tongues and ledges are held in this position by an injection release ring 28. Inside the plunger rod, an injection spring 88 is arranged compressed between a proximal wall of the plunger 30 and a distal wall part of the activation housing 34. The activation housing is further arranged with outwardly extending protrusions arranged on flexible arms 44. Abutting the outwardly extending protrusions is a retraction release ring 46. A spring 48, hereafter named penetration spring, is arranged between the retraction release ring 46 and a penetration sleeve 50. At the proximal end of the penetration sleeve 50, a retraction spring retainer 52 is snap fitted with the penetration sleeve 50 by outwardly directed protrusions 54 having a straight part and a ramped part, extending into recesses 56 of the sleeve. Outside the penetration sleeve a lockout sleeve 58 is coaxially arranged. At the rear part of the lockout sleeve 58 recesses 60 are arranged adjacent flexible arms 62 of the penetration sleeve, which arms are arranged with outwardly extending protrusions as well as inwardly extending ledges. In the initial position these ledges are in contact with a circumferential groove 68 on the activation housing. The upper part of the arms 62 is further arranged with inclined surfaces. At the upper end of the housing 10 an activation button 72 is slidably arranged, having axial extending parts 74, which are arranged with inclined surfaces facing the inclined surfaces of the arms 62.

Figure 3:
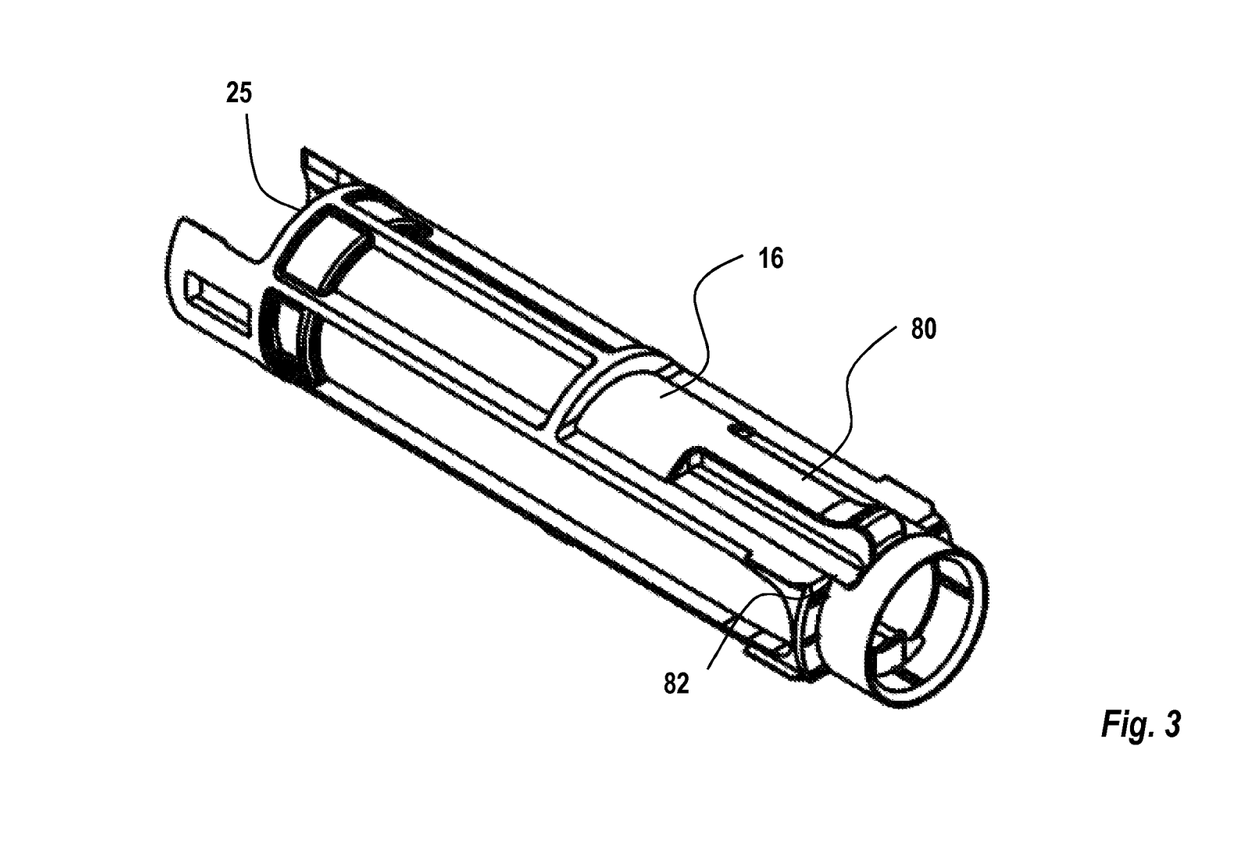
FIG. 3 shows a detailed view of a medicament container holder according to the present invention, FIG. 4 front view of the holder of FIG. 3.
Figure 4:
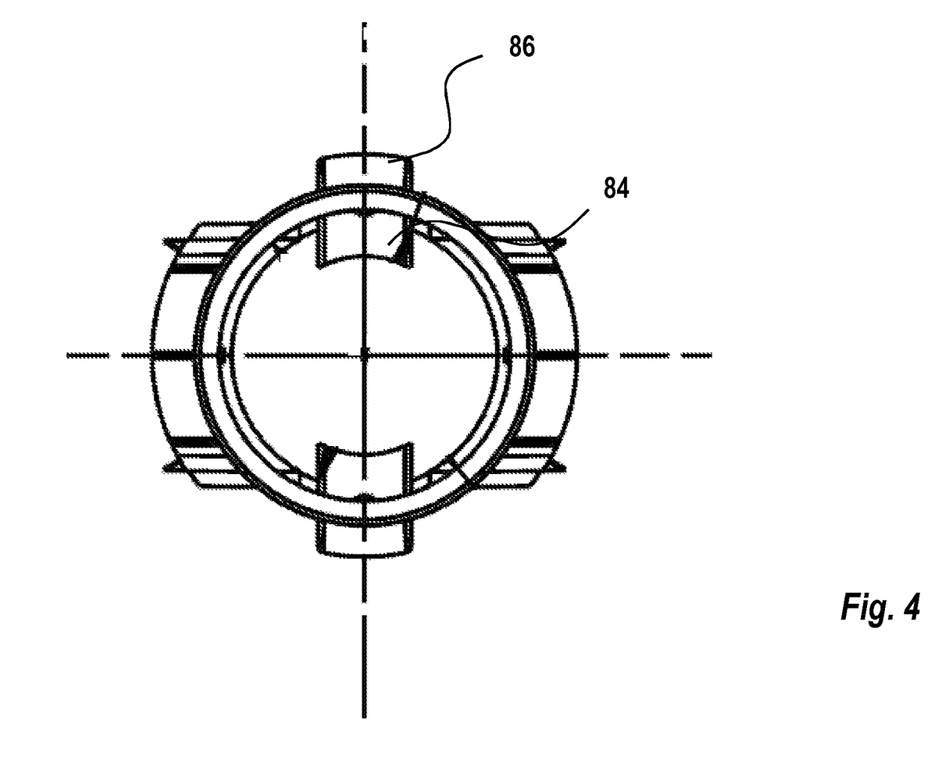
Figure 5:
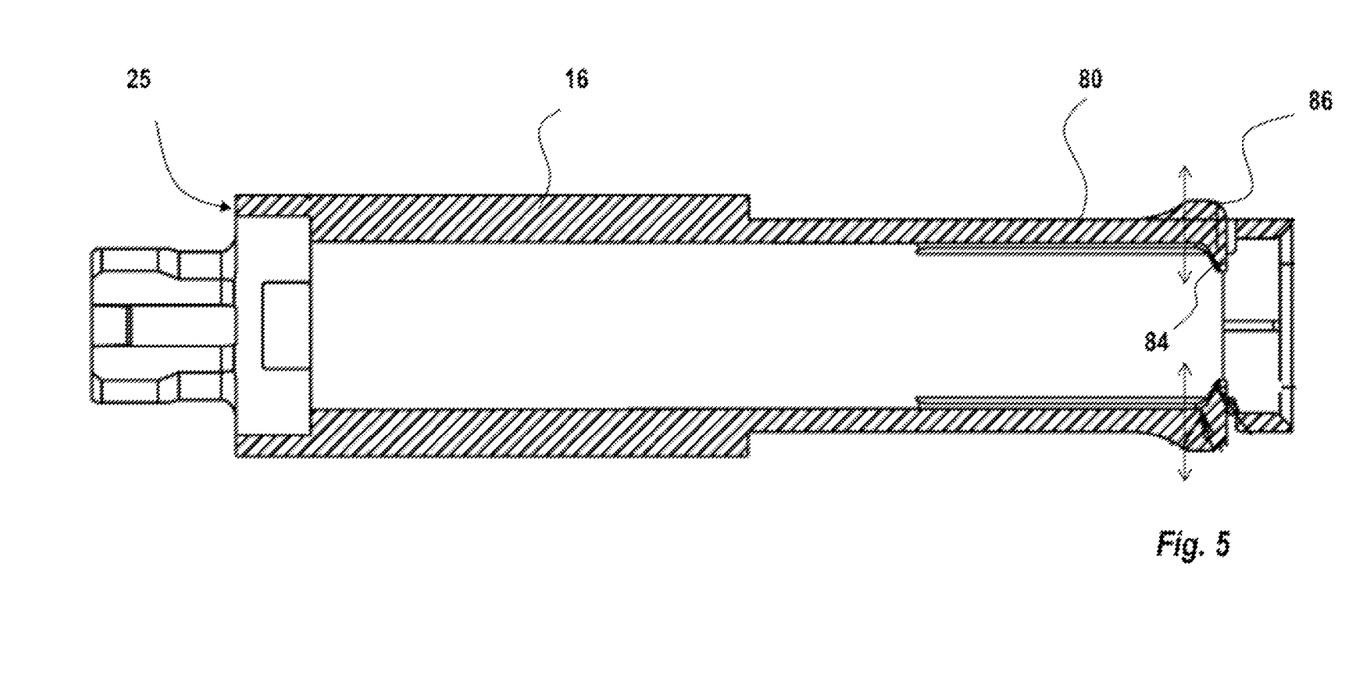
FIG. 5 shows a cross-sectional view taken along line V-V of FIG. 4.

The medicament container holder 16 has a tubular shape comprising a circumferential and longitudinal extending surface provided with a number of holders which are axially extending flexible arms 80 arranged in the material of the holder. U-shaped through-going slits 82 are made on the longitudinal extending surface of the holder 16 such that the arms 80 are directed in the proximal direction. The ends of the flexible arms 80 are arranged with generally radially inwardly directed ledges 84 that are intended to cooperate with the neck of the medicament container. Further the ends of the arms 80 are also provided with radially outwardly directed ledges 86.

In use, when a medicament container 18 is to be placed in the medicament container holder 16, the resilient support element 23 is arranged on the container abutting the flanges and the container is pushed into the container holder 16 from the distal end and towards the proximal end of the medicament container holder 16. Alternatively, the cushioning element is integrally attached to the support surfaces 25 and the container is pushed into the container holder 16 from the distal end and towards the proximal end of the medicament container holder 16.

When the rigid needle shield 20 at the proximal end of the medicament container comes in contact with the inwardly directed ledges 84 of the flexible arms 80, the latter will flex outwards in the radial direction, thereby allowing the rigid needle shield 20 to pass the ledges 84. The ledges 84 will then flex back inwardly when the rigid needle shield has passed the ledges, after which the ledges come in contact with the shoulder portion of the medicament container. Further, the flanges 24 of the medicament container are now, via the resilient support element 23, in contact with the support surface 25 of the distal part of the medicament container holder. Said outwardly directed ledges 86 are arranged to cooperate with a housing part of said medicament delivery device when the container holder is positioned inside said housing part, such that said flexible members are prevented from flexing radially outwards, and thereby firmly holding said medicament container.

Should now a breakage of the glass medicament container occur during a medicament delivery process, such as an injection, due to the forces exerted by drive force means such as injection springs, the pieces of the medicament container are kept inside the medicament delivery device and do not fall out through the proximal opening of the device.

It is to be understood that the embodiments described above and shown in the drawings only are to be regarded as non-limiting examples of the invention and that it may be modified in many ways within the scope of the patent claims.

The invention claimed is:

1. A medicament container holder arrangement for a medicament delivery device, comprising:
   a medicament container holder and a medicament container configured for placement in the medicament container holder and having a rigid needle shield arranged at a proximal end of the medicament container, wherein the medicament container holder has distally arranged support surfaces for flanges on a distal part of the medicament container, and the rigid needle shield has a diameter substantially equal to a diameter of the medicament container and is configured for sterilely sealing a needle;
   holders arranged on the medicament container holder for holding the medicament container around a proximal shoulder portion thereof; and
   a resilient support element arranged between the flanges and the support surfaces, whereby the holders and the resilient support element absorb and spread forces between the medicament container and the medicament container holder.

2. The medicament container holder arrangement of claim 1, wherein the resilient support member is configured as a collar arranged around the medicament container, adjacent a proximal surface of the flanges.

3. The medicament container holder arrangement of claim 1, wherein the resilient support member is configured as a cushion integrally attached to the support surfaces.

4. The medicament container holder arrangement of claim 1, wherein the holders include flexible arms arranged such that, when a medicament container is placed in the medicament container holder from a distal end thereof and pushed forward so that the rigid needle shield comes in contact with the flexible arms, the flexible arms flex outwardly, thereby permitting passage of the needle shield, and then flex inwardly after passage of the needle shield.

5. The medicament container holder arrangement of claim 4, wherein the flexible arms include inwardly directed ledges configured for placement in contact with the shoulder portion of the medicament container.

6. The medicament container holder arrangement of claim 4, wherein the flexible arms include through-going U-shaped slits on a longitudinal extending surface of the holders.

7. The medicament container holder arrangement of claim 6, wherein the flexible arms include inwardly directed ledges configured for placement in contact with the shoulder portion of the medicament container.

8. The medicament container holder arrangement of claim 4, wherein the holders include outwardly directed ledges configured to cooperate with a housing part of the medicament delivery device, such that when the medicament container holder is placed in the housing part, the flexible arms are prevented from flexing radially outward, thereby firmly holding the medicament container.

9. The medicament container holder arrangement of claim 1, wherein the resilient support element is a flexible material.

10. The medicament container holder arrangement of claim 9, wherein the resilient support member is configured as a collar arranged around the medicament container, adjacent a proximal surface of the flanges.

11. The medicament container holder arrangement of claim 9, wherein the resilient support member is configured as a cushion integrally attached to the support surfaces.

12. The medicament container holder arrangement of claim 9, wherein the holders include flexible arms arranged such that, when a medicament container is placed in the medicament container holder from a distal end thereof and pushed forward so that the rigid needle shield comes in contact with the flexible arms, the flexible arms flex outwardly, thereby permitting passage of the needle shield, and then flex inwardly after passage of the needle shield.

13. The medicament container holder arrangement of claim 12, wherein the flexible arms include inwardly directed ledges configured for placement in contact with the shoulder portion of the medicament container.

14. The medicament container holder arrangement of claim 12, wherein the flexible arms include through-going U-shaped slits on a longitudinal extending surface of the holders.

15. The medicament container holder arrangement of claim 14, wherein the flexible arms include inwardly directed ledges configured for placement in contact with the shoulder portion of the medicament container.

16. The medicament container holder arrangement of claim 12, wherein the holders include outwardly directed ledges configured to cooperate with a housing part of the medicament delivery device, such that when the medicament container holder is placed in the housing part, the flexible arms are prevented from flexing radially outward, thereby firmly holding the medicament container.

\* \* \* \* \*